US012383516B1

(12) United States Patent
Zhang et al.

(10) Patent No.: US 12,383,516 B1
(45) Date of Patent: Aug. 12, 2025

(54) ALBUTEROL AEROSOL SUSPENSION FORMULATION FOR ORAL INHALATION WITH HIGH AMOUNT OF GREEN PROPELLANT HYDROFLUOROOLEFIN (HFO) AND FREE OF CO-SOLVENT

(71) Applicant: Amphastar Pharmaceuticals, Inc., Rancho Cucamonga, CA (US)

(72) Inventors: Jack Yongfeng Zhang, Rancho Cucamonga, CA (US); Ying Wang, Rancho Cucamonga, CA (US); Ray Lameng Lei, Rancho Cucamonga, CA (US); Mary Zi-ping Luo, Rancho Cucamonga, CA (US)

(73) Assignee: Amphastar Pharmaceuticals, Inc., Rancho Cucamonga, CA (US)

( * ) Notice: Subject to any disclaimer, the term of this patent is extended or adjusted under 35 U.S.C. 154(b) by 0 days.

(21) Appl. No.: 19/011,043

(22) Filed: Jan. 6, 2025

(51) Int. Cl.
*A61K 31/137* (2006.01)
*A61K 9/00* (2006.01)
(Continued)

(52) U.S. Cl.
CPC .......... *A61K 31/137* (2013.01); *A61K 9/0075* (2013.01); *A61K 47/06* (2013.01);
(Continued)

(58) Field of Classification Search
CPC .... A61K 31/137; A61K 9/0075; A61K 47/05; A61K 47/26; A61K 47/32; A61K 47/34; A61K 47/39
See application file for complete search history.

(56) References Cited

U.S. PATENT DOCUMENTS 9,114,164 B2   8/2015  Corr et al.
9,308,199 B2   4/2016  Knopeck et al.
(Continued)

FOREIGN PATENT DOCUMENTS

GB   2456028 A   *  1/2009
WO   2023212191 A1  11/2023
WO   2024033941 A1   2/2024

OTHER PUBLICATIONS

Paul B. Myrdal, et al., "Advances in Metered Dose Inhaler Technology: Formulation Development," AAPS PharmSciTech, vol. 15, No. 2, Apr. 2014 [22 Pages].
(Continued)

*Primary Examiner* — Carlos A Azpuru
(74) *Attorney, Agent, or Firm* — IceMiller LLP (57) ABSTRACT

Pharmaceutical aerosol formulations containing pre-micronized albuterol sulfate, high amount of green propellant trans-1,3,3,3-tetrafluoropropene (HFO-1234ze(E)), and a surfactant (polysorbate 80 (polyoxyethylene (20) sorbitan monooleate), polysorbate 20 (polyoxyethylene (20) sorbitan monolaurate), polyethylene glycol 1000, span 85 (sorbitan trioleate), polyvinylpyrrolidone K25, or their combination) in a pressurized metered dose inhaler are described. The formulations do not use any co-solvent, i.e., they are co-solvent-free (e.g., free of ethanol, glycerol, propylene glycol, and a combination thereof). The formulations provide highly efficient delivery, through metered dose inhaler (MDI), of pre-micronized albuterol particles into the patients' respiratory tracts and have the advantages of high efficacy, improved safety, and a low global warming potential (GWP) for environmental impact.

20 Claims, 3 Drawing Sheets

(51) Int. Cl.
*A61K 47/06* (2006.01)
*A61K 47/26* (2006.01)
*A61K 47/32* (2006.01)
*A61K 47/34* (2017.01)

(52) U.S. Cl.
CPC .............. *A61K 47/26* (2013.01); *A61K 47/32* (2013.01); *A61K 47/34* (2013.01)

(56) References Cited

U.S. PATENT DOCUMENTS

| | | |
|---|---|---|
| 9,517,216 B2 | 12/2016 | Corr et al. |
| 10,959,965 B2 | 3/2021 | Corr et al. |
| 2006/0269484 A1* | 11/2006 | Knopeck ................ A61P 37/08 514/649 |
| 2021/0244688 A1 | 8/2021 | Noakes et al. |
| 2023/0080276 A1 | 3/2023 | Zambelli |
| 2023/0347080 A1 | 11/2023 | Zambelli |
| 2024/0252432 A1 | 8/2024 | Joshi et al. |

OTHER PUBLICATIONS

Chris Baron, et al., "Investigating the Propellant Pathways Leading to a Sustainable Future for MDIS," Aptar Pharma, www.ondrugdelivery. com, 2022 [5 Pages].

* cited by examiner

ALBUTEROL AEROSOL SUSPENSION FORMULATION FOR ORAL INHALATION WITH HIGH AMOUNT OF GREEN PROPELLANT HYDROFLUOROOLEFIN (HFO) AND FREE OF CO-SOLVENT

TECHNICAL FIELD

The present invention pertains to pharmaceutical aerosol formulations for the delivery of medications suitable for administration to the respiratory tract. More particularly, the present invention pertains to co-solvent-free suspension formulations containing albuterol sulfate or other pharmaceutically acceptable salt or albuterol base thereof, a surfactant, and a hydrofluoroolefin (HFO) green propellant for use in a pressurized metered dose inhaler (MDI) to treat or prevent bronchospasm (e.g., asthma or COPD).

BACKGROUND OF THE INVENTION

Medications for the treatment of respiratory disorders are commonly administered by inhalation through the mouth or nose in an aerosol formulation. One such medication is albuterol. Albuterol is approved for the treatment or prevention of bronchospasm or prevention of exercise-induced bronchospasm with the use of a propellant in a pressurized metered dose inhaler (MDI). The formulation for inhalable albuterol has gone through levels of change and development over the years in response to environmental concerns connected to the use of different propellants.

Albuterol sulfate chlorofluorocarbons (CFCs) inhalers were phased out in the United States after Dec. 31, 2008, due to the Montreal Protocol, an international agreement to reduce the use of ozone-depleting substances like CFCs. Hydrofluoroalkanes (HFAs), which have similar properties to CFC propellants, are more environmentally friendly propellants that replaced CFC. HFA-134a and HFA-227 are the two major HFA propellants in the current pressurized MDI market. There are three U.S. FDA-approved brand-name albuterol sulfate HFA inhalers available on the market, which are ProAir HFA, Proventil HFA, and Ventolin HFA.

Although HFAs do not damage the atmospheric ozone layer, they are formidable greenhouse gases that absorb infrared radiation and trap heat in the Earth's atmosphere resulting in a rise in global temperatures via the greenhouse effect. The high global warming potentials (GWP) of HFA propellants contribute to climate change. As a result, the U.S. Environmental Protection Agency has adopted an allowance allocation program to phase down the current production and consumption levels of pressurized MDI propellants such as HFA-134a and HFA-227, for which the GWP are 1,300 and 2,900, respectively (See Table 1).

Hydrofluoroolefins (HFOs), specifically 1,3,3,3-tetraflouropropene (HFO-1234ze(E)) has been suggested as one of replacement MDI propellants for HFA-134a and HFA-227 due to its low global warming potential of 6 as reported in U.S. Pat. No. 9,308,199 to Knopeck, et al. The propellant HFO-1234ze(E) is considered to be a suitable alternative for pressurized MDI formulations as it demonstrates similar physical properties (density, vapor pressure, moisture solubility, dipole moment) to HFA-134a and HFA-227 (see Table 1). Since Knopeck et al., HFOs have been explored as potential alternative propellants. For example, Baron and Shur note that "the leading propellant options for the next generation of low-GWP MDIs are HFA-152a and HFO-1234ze from the hydrofluoroolefin family." Baron and Shur, *ONdrugDeiivery*, 131, 49-52 (April 2022). Much work has already been carried out by industry stakeholders to evaluate these gases for the use as propellants in pressurized MDI products, including albuterol inhalers. However, thus far, no HFO-based albuterol inhalers have been approved by the FDA.

U.S. Pat. Nos. 9,114,164; 9,517,216; 10,959,965; and U.S. Published Application 2021/0244688A1 disclose aerosol composition of albuterol sulfate with HFA-152a. WO 2024/033941A1 discloses aerosol composition of albuterol sulfate with HFA-152a and/or HFO-1234ze(E), ethanol, and oleic acid. WO 2023/212191A1 discloses aerosol composition of albuterol and budesonide in HFO and/or HFC propellant with a suspension medium of phospholipid.

Other patent applications about HFO as MDI propellants include: U.S. Published Application 2024/0252432A1, which discloses aerosol suspension composition of glycopyrrolate, formoterol, budesonide, roflumilast in HFO-1234ze and a suspension medium of phospholipid; U.S. Published Application 2023/0347080A1, which discloses an aerosol formulation comprising formoterol and beclomethasone dipropionate in HFO propellant; and U.S. Published Application 2023/0080276 A1, which discloses an aerosol formulation comprising formoterol and beclomethasone dipropionate and glycopyrronium bromide in HFO propellant.

MDI formulations often utilize co-solvents in order to increase drug or excipient solubility. Co-solvents can also improve valve function. The use of co-solvents, such as ethanol, however, has the potential for unfavorable effects. One such effect is the increased potential for leachable and extractable impurities resulting from the reaction between the co-solvent and gasket, plastic components of the valve, and the coating of the container if any. Another possible consequence of the use of co-solvents, such as ethanol, is increased risk of flammability. In addition, certain co-solvents have a potential for allergic interactions. For example, propylene glycol, a common co-solvent, is a known allergen. Furthermore, co-solvents may not be soluble in HFO. In particular, glycerin and propylene glycol are not soluble in HFO and cannot generate stable suspension formulations.

Accordingly, what is needed is a new albuterol sulfate MDI aerosol formulation with a low GWP, free of co-solvent, and showing similar efficacy and safety as albuterol sulfate HFA inhalers.

TABLE 1

| Physicochemical and Environmental Properties of HFA and HFO Propellants | | | | | |
|---|---|---|---|---|---|
| | | Propellant | HFA-134a | HFA-227 | HFO-1234ze(E) |
| Chemical Properties | Chemical Name and Structure | | 1,1,1,2-Tetrafluoroethane | 1,1,1,2,3,3,3-Heptafluoropropane | Trans-1,3,3,3-Tetrafluoropropene |

TABLE 1-continued

Physicochemical and Environmental Properties of HFA and HFO Propellants

| | Propellant | HFA-134a | HFA-227 | HFO-1234ze(E) |
|---|---|---|---|---|
| | MW | 102.0 | 170.0 | 114.0 |
| | Liquid Density at 20° C. (g/mL) | 1.21 | 1.41 | 1.19 |
| | Dipole Moment (debye) | 2.06 | 0.93 | 1.44 |
| | Boiling Point (° C.) | −25.8 | −17.3 | −19.0 |
| | Vapor Pressure at 20° C. (psi) | 83.0 | 56.6 | 46.4 |
| | Viscosity at 20° C. (cP) | 0.20 | 0.26 | 0.19 |
| | Water solubility (ppm) | 1100 at 25° C. | 610 at 25° C. | 225 at 20° C. |
| | Log P (octanol/water) | 1.1 | 2.1 | 1.3 |
| Environmental Effects | Ozone Depletion Potential | 0 | 0 | 0 |
| | Atmospheric Life | 14.6 years | 36.5 years | 16.4 days |
| | Global Warming Potential | 1300 | 2900 | 6 |

SUMMARY OF THE INVENTION

The instant disclosure provides co-solvent-free pharmaceutical aerosol suspension formulations of albuterol sulfate in HFO-1234ze(E) suitable for administration by inhalation utilizing a pressurized MDI. The formulations contain a therapeutically effective amount of pre-micronized albuterol sulfate or other pharmaceutically acceptable salt or albuterol base thereof for the treatment or prevention of asthma and chronic obstructive pulmonary disease (COPD).

The formulations are suspensions used in a pressurized MDI and essentially contain pre-micronized albuterol sulfate particles suspended in a solution of hydrofluoroolefin (HFO) propellant and surfactant, without any co-solvent or without any co-solvent selected from the group of ethanol, glycerol, propylene glycol, and a combination thereof. The propellant typically includes trans-1,3,3,3-tetrafluoropropene, also known as HFO-1234ze(E). In certain embodiments, the preferred surfactant is polysorbate 80 (polyoxyethylene (20) sorbitan monooleate), polysorbate 20 (polyoxyethylene (20) sorbitan monolaurate), polyethylene glycol 1000 (PEG 1000), polyvinylpyrrolidone K25 (PVP K25), span 85 (sorbitan trioleate), or combinations thereof. Without being bound by theory, the surfactant is present in an amount sufficient to prevent agglomeration or flocculation of the drug particles and to maintain the physical stability of the suspension.

An object of the disclosure is to provide a comparable inhalable albuterol HFO suspension formulation to albuterol sulfate HFA formulations that is capable of effective delivery of albuterol sulfate molecules to a therapeutic site with similar or better efficacy and safety.

Another object of the disclosure is to provide a suspension formulation containing albuterol sulfate, a surfactant, and an HFO propellant that is suitable for delivery in a pressurized MDI and exhibits a uniform dosing level that is reproducible over the life of the inhaler and is alcohol-free.

In one embodiment, the co-solvent-free pharmaceutical aerosol formulation for use with a pressurized metered dose inhaler (MDI) contains a suspension of pre-micronized albuterol sulfate or other pharmaceutically acceptable albuterol salt or albuterol base thereof; a pressurized, liquefied propellant comprising a hydrofluoroolefin (HFO) (e.g. HFO-1234ze(E)) in an amount of 99.0-99.9% relative to the total weight of the formulation; and a surfactant in an amount not more than 0.1% w/w relative to the total weight of the formulation. The formulation does not contain a co-solvent selected from the group of ethanol, glycerol, propylene glycol, and a combination thereof. Alternatively, the formulation does not contain any co-solvent.

In another embodiment, the pre-micronized albuterol sulfate or a pharmaceutically acceptable salt, or albuterol base thereof has a particle size in a range of less than 5 μm in diameter and/or is present in an amount of from about 0.10% to about 0.80% (w/w) relative to the total weight of the formulation.

A variety of surfactants may be used, such as polysorbates, polyethylene glycols, sorbitan esters, polyvinylpyrrolidones, oleic acids, lecithins, and a combination thereof. In one embodiment, the surfactant is selected from the group consisting of a polysorbate, a polyethylene glycol, a sorbitan ester, a polyvinylpyrrolidone, or a combination thereof. In certain preferred embodiments the surfactant is polysorbate 80 (polyoxyethylene (20) sorbitan monooleate), polysorbate 20 (polyoxyethylene (20) sorbitan monolaurate), PEG 1000, span 85 (sorbitan trioleate), PVP K25, or combinations thereof which may be present in an amount of not more than 0.1% w/w, relative to the total weight of the formulation.

In one embodiment, the surfactant is polysorbate 80 (polyoxyethylene (20) sorbitan monooleate) or polysorbate 20 (polyoxyethylene (20) sorbitan monolaurate). In another embodiment, the polysorbate 80 (polyoxyethylene (20) sorbitan monooleate) or polysorbate 20 (polyoxyethylene (20) sorbitan monolaurate) is present in an amount of not more than 0.1% (w/w) relative to the total weight of the formulation.

In an alternative embodiment, the polyethylene glycol is PEG 1000, and is present in an amount of not more than 0.1% (w/w) relative to the total weight of the formulation. In yet another embodiment, the sorbitan ester is span 85 (sorbitan trioleate) and is present in an amount of not more than 0.05% (w/w) relative to the total weight of the formulation. In another embodiment, the polyvinylpyrrolidone is polyvinylpyrrolidone K25 and is present in an amount of not more than 0.005% (w/w) relative to the total weight of the formulation.

Specific embodiments of co-solvent-free pharmaceutical aerosol formulation are described below. Each of these embodiments do not contain a co-solvent selected from the group of ethanol, glycerol, propylene glycol, and a combination thereof. Furthermore, in each of these embodiments, the suspension formulation is a suspension formulation of pre-micronized albuterol sulfate or a pharmaceutically acceptable salt, or albuterol base thereof.

One embodiment is a co-solvent-free pharmaceutical aerosol formulation containing: the suspension formulation of pre-micronized albuterol sulfate or a pharmaceutically acceptable salt or albuterol base thereof in an amount of from about 0.10% to about 0.80% (w/w) relative to the total weight of the formulation ("RTWF"); HFO-1234ze(E) present in an amount of 99.0% to 99.9% (w/w) RTWF; and polysorbate 80 (polyoxyethylene (20) sorbitan monooleate) or polysorbate 20 (polyoxyethylene (20) sorbitan monolaurate) in an amount not more than 0.1% (w/w) RTWF.

Another embodiment is a co-solvent-free pharmaceutical aerosol formulation containing: the suspension formulation of pre-micronized albuterol sulfate or a pharmaceutically acceptable salt or albuterol base thereof in an amount of from about 0.16% to about 0.40% (w/w) RTWF; HFO-1234ze(E) present in an amount of from about 99.5% to about 99.8% (w/w) RTWF; and polysorbate 80 (polyoxyethylene (20) sorbitan monooleate) or polysorbate 20 (polyoxyethylene (20) sorbitan monolaurate) in an amount not more than 0.05% (w/w) RTWF.

Yet another embodiment is a co-solvent-free pharmaceutical aerosol formulation containing: the suspension formulation of pre-micronized albuterol sulfate or a pharmaceutically acceptable salt or albuterol base thereof in an amount of from about 0.10% to about 0.80% (w/w) RTWF; HFO-1234ze(E) present in an amount of 99.0% to 99.9% (w/w) RTWF; and PEG 1000 in an amount not more than 0.1% (w/w) RTWF.

A further embodiment is a co-solvent-free pharmaceutical aerosol formulation containing: the suspension formulation of pre-micronized albuterol sulfate or a pharmaceutically acceptable salt or albuterol base thereof in an amount of from about 0.16% to about 0.40% (w/w) RTWF; HFO-1234ze(E) present in an amount of from about 99.5% to about 99.8% (w/w) RTWF; and PEG 1000 in an amount not more than 0.02% (w/w) RTWF.

An additional embodiment is a co-solvent-free pharmaceutical aerosol formulation containing: the suspension formulation of pre-micronized albuterol sulfate or a pharmaceutically acceptable salt or albuterol base thereof in an amount of from about 0.10% to about 0.80% (w/w) RTWF; HFO-1234ze(E) present in an amount of 99.0% to 99.9% (w/w) RTWF; and span 85 (sorbitan trioleate) in an amount not more than 0.05% (w/w) RTWF.

A further embodiment is a co-solvent-free pharmaceutical aerosol formulation containing: the suspension formulation of pre-micronized albuterol sulfate or a pharmaceutically acceptable salt or albuterol base thereof in an amount of from about 0.16% to about 0.40% (w/w) RTWF; HFO-1234ze(E) present in an amount of 99.5% to about 99.8% (w/w) RTWF; and span 85 (sorbitan trioleate) in an amount not more than 0.01% (w/w) RTWF.

An additional embodiment is a co-solvent-free pharmaceutical aerosol formulation containing: the suspension formulation of pre-micronized albuterol sulfate or a pharmaceutically acceptable salt or albuterol base thereof in an amount of from about 0.10% to about 0.80% (w/w) RTWF; HFO-1234ze(E) present in an amount of 99.0% to 99.9% (w/w) RTWF; and polyvinylpyrrolidone K25 in an amount not more than 0.005% (w/w) RTWF.

Another embodiment is a co-solvent-free pharmaceutical aerosol formulation containing: the suspension formulation of pre-micronized albuterol sulfate or a pharmaceutically acceptable salt or albuterol base thereof in an amount of from about 0.16% to about 0.40% (w/w) RTWF; HFO-1234ze(E) present in an amount of 99.5% to 99.8% (w/w) RTWF; and polyvinylpyrrolidone K25 in an amount not more than 0.005% (w/w) RTWF.

The disclosure also includes a pressurized metered dose inhaler containing the co-solvent free formulations. In one embodiment, the pressurized metered dose inhaler has a canister filled with the co-solvent-free pharmaceutical aerosol formulation of the disclosures, a valve, an actuator having a mouthpiece, and a dose indicator.

Other features and advantages of the invention will be apparent from the detailed description and examples that follow.

BRIEF DESCRIPTION OF THE DRAWINGS

The foregoing summary, as well as the following detailed description of the invention, will be better understood when read in conjunction with the appended figures. For the purpose of illustrating the invention, the figures demonstrate embodiments of the present invention. It should be understood, however, that the invention is not limited to the precise arrangements, examples, and instrumentalities shown.

DETAILED DESCRIPTION

This disclosure is based on the discovery of albuterol sulfate suspension formulations for MDIs, which avoid environmental concerns associated with albuterol sulfate HFA. These suspension formulations provide comparable efficacy and safety of respirable drug delivery to that of albuterol sulfate HFA while utilizing HFO propellant with a much lower GWP than HFA and a near-zero global warming effect.

In certain embodiments, this disclosure provides specific albuterol sulfate MDI formulations utilizing trans-1,3,3,3-tetrafluoropropene (HFO-1234ze(E)) as a medical propellant, a surfactant, and are free of a co-solvent.

Without being bound by theory, it is thought that the formulations of the disclosure provide at least the following advantages:

the albuterol sulfate suspension formulations utilize the more environmentally friendly HFO propellant to fulfill the requirements of the Montreal Protocol while maintaining comparable efficacy and safety effects of the previous albuterol sulfate HFA formulation; and the albuterol sulfate HFO formulations are free of co-solvent, such as ethanol, which avoided the leachable and extractable impurities caused by co-solvent, and also reduced the formulation flammability.

The purpose of the present disclosure is to demonstrate greater mindfulness in working towards the goal of mitigating the effects of global warming by providing an inhalable albuterol sulfate suspension aerosol formulation for delivery to the pulmonary air passages with a near-zero global warming potential (GWP). More specifically, in the preferred compositions, the propellant of the present invention has a negligible contribution to ozone depletion and has a very low contribution to global warming compared to HFAs, such as HFA-134a and HFA-227. In addition, the low GWP propellant of HFO-1234ze(E) does not have a substantially negative effect on the atmospheric environment and chemistry.

The general description and the following detailed description are exemplary and explanatory only and are not restrictive of the invention, as defined in the appended claims. Other aspects of the present invention will be apparent to those skilled in the art given the detailed description of the invention as provided herein.

For clarity of disclosure, and not by way of limitation, the detailed description of the invention is divided into subsections that describe or illustrate certain features, embodiments, or applications of the present invention.

Definitions

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods, and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates, which may need to be independently confirmed.

It is noted that, as used herein and in the appended claims, the singular forms "a," "an," and "the" include plural referents unless the context clearly dictates otherwise. It is further noted that the claims may be drafted to exclude any optional element. As such, this statement is intended to serve as an antecedent basis for the use of such exclusive terminology as "solely," "only" and the like in connection with the recitation of claim elements or use of a "negative" limitation.

Each of the individual embodiments described and illustrated herein has discrete components and features that may be readily separated from or combined with the features of any of the other several embodiments without departing from the scope or spirit of the present invention. Any recited method can be carried out in the order of events recited or in any other order which is logically possible.

As used herein, the term "about" when referring to a measurable value such as an amount, a temporal duration, and the like, is meant to encompass variations of ±20% or ±10%, more preferably +5%, even more preferably +1%, and still more preferably +0.1% from the specified value, as such variations are appropriate to perform the disclosed methods.

It is also to be understood that the terminology used herein is for the purpose of describing particular embodiments only and is not intended to be limiting.

As used herein, the terms "comprising," "including," "containing" and "characterized by" are exchangeable, inclusive, and open-ended and do not exclude additional, unrecited elements or method steps. Any recitation herein of the term "comprising," particularly in a description of components of a composition or in a description of elements of a device, is understood to encompass those compositions and methods consisting essentially of and consisting of the recited components or elements.

Throughout this specification, unless the context requires otherwise, the word "comprise" or variations such as "comprises" or "comprising," will be understood to imply the inclusion of a stated integer or group of integers but not the exclusion of any other integer or group of integers.

As used herein, the term "consisting of" excludes any element, step, or ingredient not specified in the claim element.

Before certain embodiments are described in greater detail, it is to be understood that this invention is not limited to certain embodiments described, as such may, of course, vary. It is also to be understood that the terminology used herein is for the purpose of describing certain embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

It is also to be understood that the terminology used herein is for the purpose of describing particular embodiments only and is not intended to be limiting.

A "subject" or "patient," as used herein, may be a human or non-human mammal. Non-human mammals include, for example, livestock and pets, such as ovine, bovine, porcine, canine, feline, and murine mammals. Preferably, the subject is a human.

As used herein, and as well-understood in the art, "treatment" is an approach for obtaining beneficial or desired results, including clinical results. For purposes of this invention, beneficial or desired clinical results include, but are not limited to, alleviation or amelioration of one or more symptoms, diminishment of the extent of disease, stabilized (i.e., not worsening) state of disease, preventing the spread of disease, delay or slowing of disease progression, amelioration or palliation of the disease state, and remission (whether partial or total), whether detectable or undetectable. "Treatment" can also mean prolonging survival as compared to expected survival if not receiving treatment.

As used herein, the term "HFO" refers to hydrofluoroolefin. The term "HFOs" refers to hydrofluoroolefins.

As used herein, the term "HFO-1234ze" refers to 1,3,3, 3-tetraflouropropene or trans-1,3,3,3-tetraflouropropene or trans-HFOze. The structure of HFO-1234ze is shown in Table 1 above. Furthermore, as used herein, "HFO-1234ze (E)" is synonymous with "HFO-1234ze".

As used herein, the term "MDI" refers to a metered dose inhaler.

Pharmaceutical Aerosol Formulations

One aspect of the disclosure is directed to co-solvent-free pharmaceutical aerosol formulations for use with a pressurized metered dose inhaler that contains albuterol sulfate or other pharmaceutically acceptable salt or albuterol base thereof, as the active pharmaceutical ingredient (API) and a pressurized, liquefied propellant containing a hydrofluoroolefin (HFO).

The pharmaceutical aerosol formulations of the disclosure do not require the addition of a co-solvent, i.e., they are albuterol formulations without a co-solvent (devoid of a co-solvent). Accordingly, the formulations of the disclosure do not comprise or do not contain a co-solvent; they are co-solvent-free or without a co-solvent. In certain embodiments, the formulations do not comprise or do not contain a co-solvent selected from the group consisting of ethanol, glycerol, propylene glycol, and a combination thereof. In certain embodiments, the formulations do not contain (are devoid of), i.e. lack, a co-solvent, such as ethyl alcohol, isopropyl alcohol, glycerol, propylene glycol, ethylene glycol, propane, butane, isobutene, pentane, dimethyl ether, diethyl ether, and a combination thereof. In further embodiments, the formulations do not comprise or do not contain any co-solvent.

In certain embodiments, the formulations are administered from a pressurized metered-dose inhaler (MDI) having a canister, a valve, an actuator, and a dose indicator. In one embodiment, the canister is a fluorocarbon polymer-coated canister.

The co-solvent-free pharmaceutical aerosol formulations of the disclosure include at least three different components: (a) a drug component (e.g. a suspension formulation of pre-micronized albuterol sulfate or other pharmaceutically acceptable salt, or albuterol base thereof); (b) a propellant component; and (c) a surfactant component. The drug component includes the active pharmaceutical ingredient. One embodiment of the disclosure is a pharmaceutical aerosol formulation for use with a pressurized metered dose inhaler containing: a suspension formulation of pre-micronized albuterol sulfate or other pharmaceutically acceptable salt or albuterol base thereof as the drug component; a pressurized, liquefied propellant comprising a hydrofluoroolefin as the propellant component; and a surfactant in an amount not more than about 0.1% (w/w) relative to the total weight of the formulation as the surfactant component.

The pharmaceutical compositions of the present invention typically contain 0.10%-0.80% w/w of the drug component, 99.0%-99.9% w/w of the propellant component, and not more than 0.1% w/w of the surfactant component. Preferred compositions contain from 0.16% to 0.40% w/w of the drug component, from 99.5% to 99.8% w/w of the propellant component, and not more than 0.05% w/w of the surfactant component. All percentages are based on the total weight of the pharmaceutical compositions.

In certain embodiments, the inhalable pharmaceutical suspension aerosol includes albuterol sulfate as the active pharmaceutical ingredient, a propellant of hydrofluoroolefin, and a surfactant.

Drug Component

The drug component of the formulations of the disclosure generally is a suspension formulation of pre-micronized albuterol sulfate or other pharmaceutically acceptable salt, or albuterol base thereof. The active ingredient of micronized albuterol sulfate or albuterol base is generally present in a therapeutically effective amount to exert the intended therapeutic action.

In certain embodiments, the aerosol suspension (i.e., the pharmaceutical aerosol formulation) contains from about 0.10% to about 0.80% w/w, preferably from about 0.16% to 0.40% w/w, alternatively from about 0.16% to about 0.80% w/w, alternatively from about 0.20% to about 0.80% w/w, alternatively from about 0.20% to about 0.75% w/w, alternatively from about 0.20% to about 0.50% w/w, from about 0.20% to about 0.40% w/w of albuterol sulfate relative to the total weight of the suspension.

The formulations of the disclosure contain albuterol sulfate as the active pharmaceutical ingredient (API) with a dose strength from about 60 mcg to about 200 mcg. In one embodiment, the preferred albuterol dose strength is in the range of about 60 mcg to about 120 mcg.

The particle size of the particular (e.g., micronized) albuterol sulfate or other pharmaceutically acceptable salts or albuterol base thereof should be such that to permit inhalation of substantially all the drug into the lungs upon administration of aerosol formulation and will thus be less than 50 μm in terms of volume mean diameter (VMD), and in particular, in the range of from about 1 μm to about 5 μm. In certain embodiments, the preferred particle size of the micronized albuterol sulfate is from about 1 μm to 3 μm.

Propellant Component

The pharmaceutical aerosol formulations contain a hydrofluoroolefin (HFO) as the propellant to deliver the drug molecules to the lungs. HFO may be present in amounts ranging from 99.0% to 99.9% w/w, alternatively from 99.5% to 99.8% w/w, alternatively from 99.15% to 99.83% w/w relative to the total weight of the aerosol formulation.

The preferred propellant is HFO-1234ze(E). The properties for HFO-1234ze(E) are shown in Table 1 above. The amount of HFO-1234ze(E) in the formulation can range from about 99.0% to about 99.9% w/w, alternatively from 99.15% to 99.83% w/w relative to the total weight of the aerosol formulation. In some embodiments, the HFO-1234ze(E) amount ranges from about 99.5% to 99.8% w/w, relative to the total weight of the aerosol formulation.

Surfactant Component

The formulations also contain a surfactant. The surfactant is present in the formulations in an amount not more than about 0.1% (w/w) relative to the total weight of the formulation. In some embodiments, the surfactant is present in an amount of about 0.005-0.05% w/w, alternatively about 0.005-0.02% w/w, alternatively about 0.005-0.1% w/w, alternatively about 0.002-0.1% w/w, alternatively about 0.01-0.05% w/w, alternatively about 0.01-0.1% w/w, alternatively about 0.001-0.005% w/w, alternatively about 0.001-0.01% w/w relative to the total weight of the aerosol formulation.

In certain embodiments, the surfactant is selected from the group consisting of polysorbates, polyethylene glycols, sorbitan esters, polyvinylpyrrolidones, oleic acid, lecithin, and a combination thereof. In one embodiment, the surfactant is a polysorbate such as polysorbate 80 (polyoxyethylene (20) sorbitan monooleate) and polysorbate 20 (polyoxyethylene (20) sorbitan monolaurate). In another embodiment, the surfactant is a polyethylene glycol such as polyethylene glycol 1000. In an alternate embodiment, the surfactant is a sorbitan ester such as span 85 (sorbitan trioleate). In yet another embodiment, the surfactant is a polyvinylpyrrolidone such as polyvinylpyrrolidone K25.

In one embodiment, the surfactant is selected from the group consisting of a polysorbate, a polyethylene glycol, a sorbitan ester, a polyvinylpyrrolidone, or a combination thereof. Alternatively, the surfactant can be selected from the group of polysorbate 80 (polyoxyethylene (20) sorbitan monooleate), polysorbate 20 (polyoxyethylene (20) sorbitan monolaurate), polyethylene glycol 1000, span 85 (sorbitan trioleate), polyvinylpyrrolidone K25, and a combination thereof.

In some embodiments, the surfactant is polysorbate 80 (polyoxyethylene (20) sorbitan monooleate) or polysorbate 20 (polyoxyethylene (20) sorbitan monolaurate). In some embodiments, polysorbate 80 (polyoxyethylene (20) sorbitan monooleate) or polysorbate 20 (polyoxyethylene (20) sorbitan monolaurate) is present in an amount of not more than about 0.1% w/w relative to the total weight of the aerosol formulation. In other embodiments, the polysorbate 80 (polyoxyethylene (20) sorbitan monooleate) amount is about 0.005-0.05% w/w, alternatively about 0.005-0.1% w/w, alternatively about 0.005-0.01% w/w relative to the total weight of the aerosol formulation.

In some embodiments, the surfactant is polyethylene glycol 1000. In some embodiments, polyethylene glycol 1000 is present in an amount of not more than about 0.1% w/w relative to the total weight of the aerosol formulation. In other embodiments, the polyethylene glycol 1000 amount is about 0.005-0.02% w/w, alternatively about 0.005-0.1% w/w, alternatively about 0.005-0.01% w/w relative to the total weight of the aerosol formulation.

In some embodiments, the surfactant is span 85 (sorbitan trioleate). In some embodiments, span 85 (sorbitan trioleate) is present in an amount of not more than 0.05% w/w relative to the total weight of the aerosol formulation. In other embodiments, the preferred span 85 (sorbitan trioleate) amount is about 0.01% w/w, alternatively about 0.01-0.05% w/w relative to the total weight of the aerosol formulation.

In some embodiments, the surfactant is polyvinylpyrrolidone K25. In some embodiments, polyvinylpyrrolidone K25 is present in an amount of not more than 0.005% w/w relative to the total weight of the aerosol formulation. In other embodiments, the polyvinylpyrrolidone K25 amount is about 0.001% w/w, alternatively about 0.001-0005% w/w relative to the total weight of the aerosol formulation.

Without being bound by theory, the amount of surfactant is thought to be to improve the suspension stability. Furthermore, without being bound by theory, the surfactant is included in the formulation to improve the physical stability of the formulation and ensure consistent delivery of medication from pressurized MDI by coating the microparticles, which, in turn, prevents agglomeration of the particles, prevents adhesion of the particles to container walls, and provides lubrication for valve components in the MDI.

Specific Embodiments of Co-Solvent-Free Pharmaceutical Aerosol Formulations

Preferred embodiments of co-solvent free pharmaceutical aerosol formulations of the disclosure are listed below. Each co-solvent free pharmaceutical aerosol formulation is at least free of, devoid of, or does not contain a co-solvent selected from the group of ethanol, glycerol, propylene glycol, and a combination thereof. Alternatively, each co-solvent free pharmaceutical aerosol formulation is at least free of, devoid of, or does not contain a co-solvent selected from the group consisting of polysorbates, polyethylene glycols, sorbitan esters, polyvinylpyrrolidones, oleic acid, lecithin, and a combination thereof. In other embodiments, each co-solvent free pharmaceutical aerosol formulation is at least free of, devoid of, or does not contain any co-solvent.

In one preferred embodiment, the co-solvent-free pharmaceutical aerosol formulation contains an effective amount of pre-micronized albuterol sulfate or a pharmaceutically acceptable salt or albuterol base thereof in an amount ranging from about 0.10% to about 0.80% w/w with particle size less than about 5 μm, HFO-1234ze(E) propellant in an amount ranging from 99.0% to 99.9% w/w, and a surfactant selected from the group comprising polysorbate 80 (polyoxyethylene (20) sorbitan monooleate), polysorbate 20 (polyoxyethylene (20) sorbitan monolaurate), polyethylene glycol 1000, span 85 (sorbitan trioleate), polyvinylpyrrolidone K25, or a combination thereof in an amount not more than 0.1% w/w relative to the total weight of the aerosol formulation.

In another preferred embodiment, the co-solvent-free pharmaceutical aerosol formulation contains an effective amount of pre-micronized albuterol sulfate or a pharmaceutically acceptable salt or albuterol base thereof in an amount ranging from about 0.16% to about 0.40% w/w with particle size less than about 5 μm, alternatively from about 1 μm to about 2 μm in diameter, HFO-1234ze(E) propellant in an amount ranging from 99.5% to 99.8% w/w, and polysorbate 80 (polyoxyethylene (20) sorbitan monooleate) or polysorbate 20 (polyoxyethylene (20) sorbitan monolaurate) in an amount of not more than 0.05% w/w relative to the total weight of the aerosol formulation.

In yet another preferred embodiment, the co-solvent-free pharmaceutical aerosol formulation contains an effective amount of pre-micronized albuterol sulfate or a pharmaceutically acceptable salt or albuterol base thereof in an amount ranging from about 0.16% to about 0.40% w/w with particle size less than about 5 μm, alternatively from about 1 μm to about 2 μm in diameter, HFO-1234ze(E) propellant in an amount ranging from 99.5% to 99.8% w/w, and polyethylene glycol 1000 in an amount of not more than 0.02% w/w relative to the total weight of the aerosol formulation.

In an alternate preferred embodiment, the co-solvent-free pharmaceutical aerosol formulation contains an effective amount of pre-micronized albuterol sulfate or a pharmaceutically acceptable salt or albuterol base thereof in an amount ranging from about 0.16% to about 0.40% w/w with particle size less than about 5 μm, alternatively from about 1 μm to about 2 μm in diameter, HFO-1234ze(E) propellant in an amount ranging from 99.5% to 99.8% w/w, and span 85 (sorbitan trioleate) in an amount of not more than 0.01% w/w relative to the total weight of the aerosol formulation.

In a further preferred embodiment, the co-solvent-free pharmaceutical aerosol formulation contains an effective amount of pre-micronized albuterol sulfate or a pharmaceutically acceptable salt or albuterol base thereof in an amount ranging from about 0.16% to about 0.40% w/w with particle size less than about 5 μm, alternatively from about 1 μm to about 2 μm in diameter, HFO-1234ze(E) propellant in an amount ranging from 99.5% to 99.8% w/w, and polyvinylpyrrolidone K25 in an amount of not more than 0.005% w/w relative to the total weight of the aerosol formulation.

The formulations of the disclosure when administered via a metered dose inhaler can be used to treat or prevent asthma and/or chronic obstructive pulmonary disease (COPD).

In addition, the disclosure includes methods of preparing the formulations. The methods generally include adding the effective amount of pre-micronized albuterol sulfate or a pharmaceutically acceptable salt or albuterol base thereof and the surfactant in a canister, enclosing the canister with a metering valve, pressurizing the container with the propellant, and mixing the formulations well through sonication and vortex.

Without further description, it is believed that one of ordinary skill in the art can, using the preceding description and the following illustrative examples, make and utilize the present invention and practice the claimed methods. The following working examples, therefore, specifically point out the preferred embodiments of the present invention and are not to be construed as limiting in any way the remainder of the disclosure.

EXAMPLES

Example 1: Formulation Description and Preparation Procedure

A number of albuterol sulfate formulations were developed to investigate the in vitro performance of albuterol sulfate in metered dose inhalers (MDIs) containing HFO-1234ze(E) and a surfactant (see Table 2). The particle size of the micronized albuterol sulfate was less than 2 μm in terms of volume mean diameter (VMD).

crimper/filler. The canister was then sonicated and mixed for 60 minutes at room temperature to ensure the dissolution of the surfactant in the propellant and the dispersion of the drug in the medium.

Formulation 1 is suitable for delivering 60 μg albuterol per actuation.

Formulations 2-9 were prepared in a manner similar to the procedure for Formulation 1 with the corresponding amounts of API, surfactant, and HFO as well as the corresponding valve. Each formulation is suitable for delivering its respective albuterol dose per actuation.

In addition, variations of Formulations 1-9 can be prepared using polysorbate 20 (polyoxyethylene (20) sorbitan monolaurate) (T20) instead of T80. The process to make these formulations was the same except that T20 is used instead of T80. Each formulation is suitable for delivering its respective albuterol dose per actuation. For example, variations of Formulations 2, 5, 8, and 9 were also prepared using T20.

Formulations 10-13 (See Table 2)

Formulation 10 contains 0.36% w/w micronized albuterol sulfate with a particle size of less than 2 μm (VMD), 0.005% w/w PEG 1000, and 99.64% w/w HFO-1234ze(E), which was prepared by:

(1) Adding 32.4 mg micronized albuterol sulfate and 0.45 mg PEG 1000 into a 14 mL fluorocarbon polymer-coated canister and crimping a 28 μL valve on it; and (2) Pressurized filling about 8.97 g HFO-1234ze(E) into the canister through the valve using a manual Pamasol crimper/filler. The canister was then sonicated and

TABLE 2

Albuterol Sulfate Aerosol Suspension Formulations

| Formulation # | pMDI Formulation, % w/w | | | API Strength, mcg | pMDI Valve Size, μL |
|---|---|---|---|---|---|
| | API Albuterol Sulfate | Surfactant | Propellant HFO-1234ze(E) | | |
| 1 | 0.24 | T80 or T20  0.01 | 99.75 | 60 | 28 |
| 2 | 0.36 | 0.01 | 99.63 | 90 | 28 |
| 3 | 0.72 | 0.05 | 99.23 | 180 | 28 |
| 4 | 0.80 | 0.05 | 99.15 | 200 | 28 |
| 5 | 0.36 | 0.005 | 99.64 | 90 | 28 |
| 6 | 0.36 | 0.05 | 99.59 | 90 | 28 |
| 7 | 0.36 | 0.1 | 99.54 | 90 | 28 |
| 8 | 0.16 | 0.01 | 99.83 | 90 | 63 |
| 9 | 0.20 | 0.01 | 99.79 | 90 | 50 |
| 10 | 0.36 | PEG 1000  0.005 | 99.64 | 90 | 28 |
| 11 | 0.36 | 0.01 | 99.63 | 90 | 28 |
| 12 | 0.36 | 0.02 | 99.62 | 90 | 28 |
| 13 | 0.36 | 0.1 | 99.54 | 90 | 28 |
| 14 | 0.36 | Span 85  0.01 | 99.63 | 90 | 28 |
| 15 | 0.36 | 0.05 | 99.59 | 90 | 28 |
| 16 | 0.36 | PVP K25  0.001 | 99.64 | 90 | 28 |
| 17 | 0.36 | 0.005 | 99.64 | 90 | 28 |

Formulations 1-9 (See Table 2)

Formulation 1 contains 0.24% w/w micronized albuterol sulfate with a particle size of less than 2 μm (VMD), 0.01% w/w polysorbate 80 (polyoxyethylene (20) sorbitan monooleate) (T80), and 99.75% w/w HFO-1234ze(E), which was prepared by:

(1) Adding 21.6 mg micronized albuterol sulfate and 0.9 mg T80 into a 14 mL fluorocarbon polymer-coated canister and crimping a 28 μL valve on it; and (2) Pressurized filling about 8.98 g HFO-1234ze(E) into the canister through the valve using a manual Pamasol mixed for 60 minutes at room temperature to ensure the dissolution of the surfactant in the propellant and the dispersion of drug in the medium.

Formulation 10 is suitable for delivering 90 μg albuterol per actuation.

Formulations 11-13 were prepared in a manner similar to the procedure for Formulation 10 with the corresponding amounts of API, surfactant, and HFO. Each formulation is suitable for delivering a 90 μg albuterol dose per actuation.

Formulations 14 and 15 (See Table 2)

Formulation 14 contains 0.36% w/w micronized albuterol sulfate with a particle size of less than 2 μm (VMD), 0.01% w/w Span 85 (sorbitan trioleate), and 99.63% w/w HFO-1234ze(E), which was prepared by:

(1) Adding 32.4 mg micronized albuterol sulfate and 0.9 mg span 85 (sorbitan trioleate) into a 14 mL fluorocarbon polymer-coated canister and crimping a 28 μL valve on it; and (2) Pressurized filling about 8.97 g HFO-1234ze(E) into the canister through the valve using a manual Pamasol crimper/filler. The canister was then sonicated and mixed for 60 minutes at room temperature to ensure the dissolution of the surfactant in the propellant and dispersion of the drug in the medium.

Formulation 14 is suitable for delivering 90 μg albuterol per actuation.

Formulation 15 was prepared in a manner similar to the procedure for Formulation 14 with the corresponding amounts of API, surfactant, and HFO. Each formulation is suitable for delivering a 90 μg albuterol dose per actuation.

Formulations 16 and 17 (See Table 2)

Formulation 16 contains 0.36% w/w micronized albuterol sulfate with a particle size of less than 2 μm (VMD), 0.001% w/w PVP K25, and 99.64% w/w HFO-1234ze(E), which was prepared by:

(1) Adding 32.4 mg micronized albuterol sulfate and 0.09 mg PVP K25 into a 14 mL fluorocarbon polymer-coated canister and crimping a 28 μL valve on it; and (2) Pressurized filling of about 8.97 g HFO-1234ze(E) into the canister through the valve using a manual Pamasol crimper/filler. The canister was then sonicated and mixed for 60 minutes at room temperature to ensure the dissolution of the surfactant in the propellant and dispersion of the drug in the medium Formulation 16 is suitable for delivering 90 μg albuterol per actuation.

Formulation 17 was prepared in a manner similar to the procedure for Formulation 16 with the corresponding amounts of API, surfactant, and HFO. Each formulation is suitable for delivering a 90 μg albuterol dose per actuation.

Example 2: In Vitro Respirable Drug Delivery Assessment of Albuterol Sulfate Suspension Formulations with HFO-1234Ze(E) Propellant The therapeutic efficacy of an aerosol formulation is determined by the amount of the drug particles that can penetrate a patient's deeper lung region, which is evaluated by an in vitro Andersen Cascade Impactor. Aerodynamic particle size distribution (APSD) by Andersen Cascade Impaction analysis is coupled with an HPLC assay per USP <601>. APSD is for the evaluation of the fine particle fractions at different stages of the lung, which has eight stages simulating the various parts of the human respiratory system (the different regions of the lung). It utilizes jet stages to classify aerosols from 9.0 μm (stage 0) to 0.4 μm (stage 7) at the flow rate of 28.3 L/min and allows drug particles to impact stainless steel impaction plates. A filter located after stage 7 collects all particles smaller than 0.4 μm.

The size of the aerosol particles that enter the device can be categorized relative to which level they are deposited into:

All particles that enter the device, thereby passing the throat and actuator, from stage 0 to the filter are categorized as impactor-sized mass (ISM). The ISM is a representative measure of the total amount of drug particles that enter the respiratory tract.

Particles that deposit in the Andersen Impactor throat to stage 2 are categorized as being of coarse particle mass (CPM) which represent particles that pass through the throat but collect in the upper airways due to their large size.

Particles that deposit in stage 3 to the filter are categorized as being of fine particle mass (FPM). The FPM range represents the particle size that is able to reach the respirable regions of the lung or the effective therapeutic regions. Having a higher FPM allows for a lower amount of total drug dose necessary to achieve equivalent therapeutic benefits.

Fine particle fraction (FPF) is a measure of the percentage of drug molecules deposited in the respirable regions of a patient's lungs ([Stage 3-filter]/Total). The FPF represents the efficiency of the respirable drug delivery.

Particles that deposit in stage 6 to the filter are categorized as being of extra-fine particle mass (EPM) which are particles that penetrate further into the respiratory tract.

The Mass Median Aerodynamic Diameter (MMAD) and Geometric Standard Deviation (GSD) are calculated based on the Andersen Cascade Impaction data and are used for the characterization of the aerodynamic size distribution of the drug particles.

Figure 1:
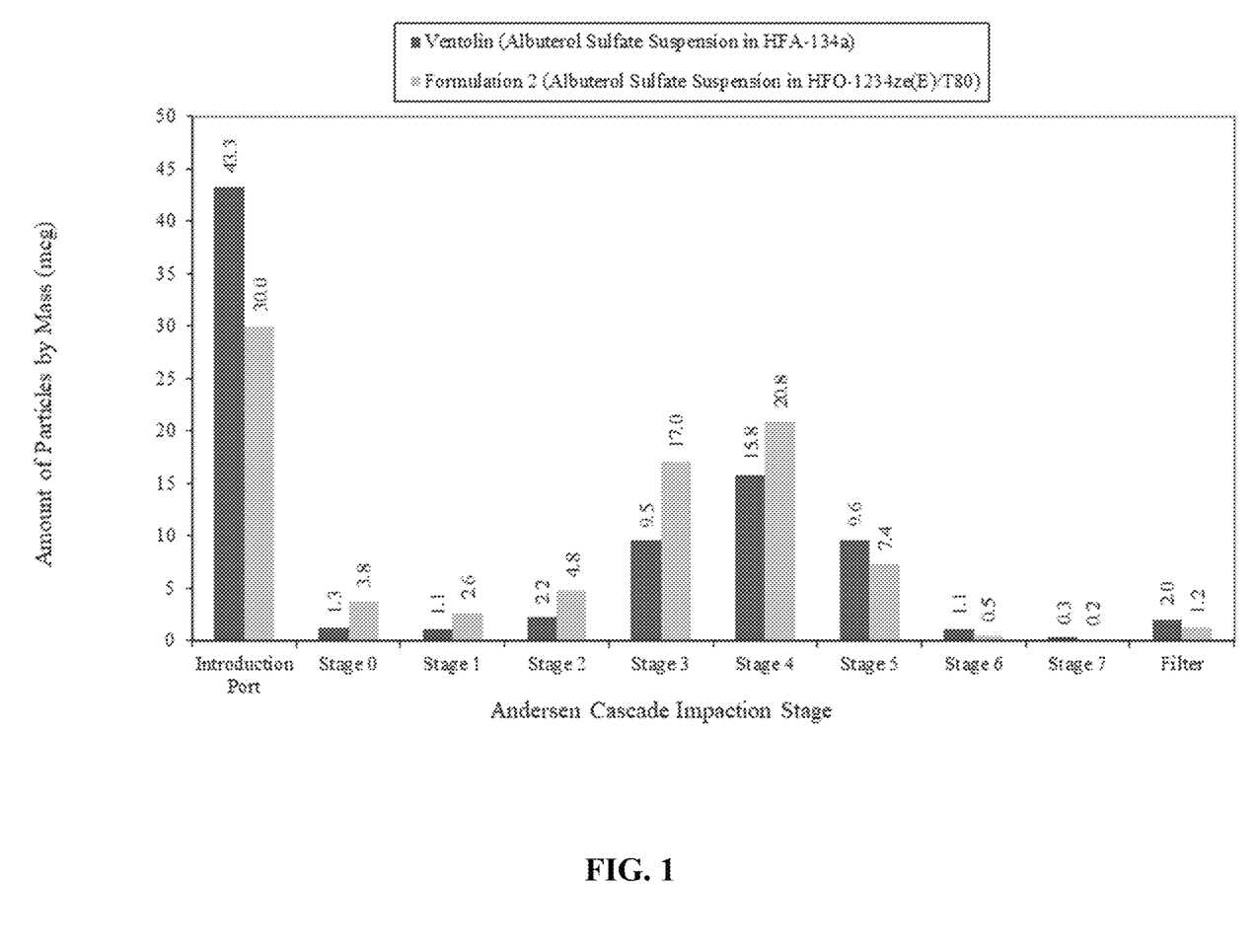
FIG. 1 is a chart showing the Andersen Cascade Impactor Stage distribution of albuterol sulfate suspension in HFO-1234ze(E) and HFA-134a Propellants.

The total emitted dose by pMDI is evaluated by Single Actuation Content (SAC) analysis, of which the sample is collected per USP <601> with Apparatus A device at the air flow rate of 28.3 L/min, followed by HPLC assay.

a. Comparison of Respirable Drug Delivery Between Formulation of Albuterol Sulfate/HFO-1234Ze(E)/Surfactant Formulations Vs. Albuterol Sulfate/HFA-134a Formulation The in vitro aerodynamic particle size distribution (APSD) by Andersen Cascade Impaction analysis and single actuation content (SAC) analysis was conducted to evaluate the performance of the disclosed albuterol sulfate/IFO MDI and to compare with the commercial albuterol sulfate HFA MDI (Ventolin HFA). The data are summarized in Table 3. The APSD by Andersen Cascade Impactor analysis of albuterol sulfate/HFO-1234ze(E)/surfactant and albuterol sulfate/HFA-134a (Ventolin HFA) are shown in FIG. 1.

The SAC data in Table 3 for albuterol sulfate from both HFA-134a formulation and HFO-1234ze(E)/Surfactant formulations was similar. The FPM, ISM, and FPF for the formulation containing HFO-1234ze(E)/Surfactant was similar to or greater than the formulation with HFA-134a (Ventolin HFA). The stage-by-stage Andersen Cascade Impaction data presented in FIG. 1 shows that the albuterol sulfate/HFO-1234ze(E)/T80 formulation had much less throat deposition and higher deposition in stage 3 and stage 4.

TABLE 3

In vitro Aerosolization Performance of Albuterol Sulfate HFO with Various Surfactant vs Albuterol Sulfate HFA (Ventolin HFA)

Figure 2:
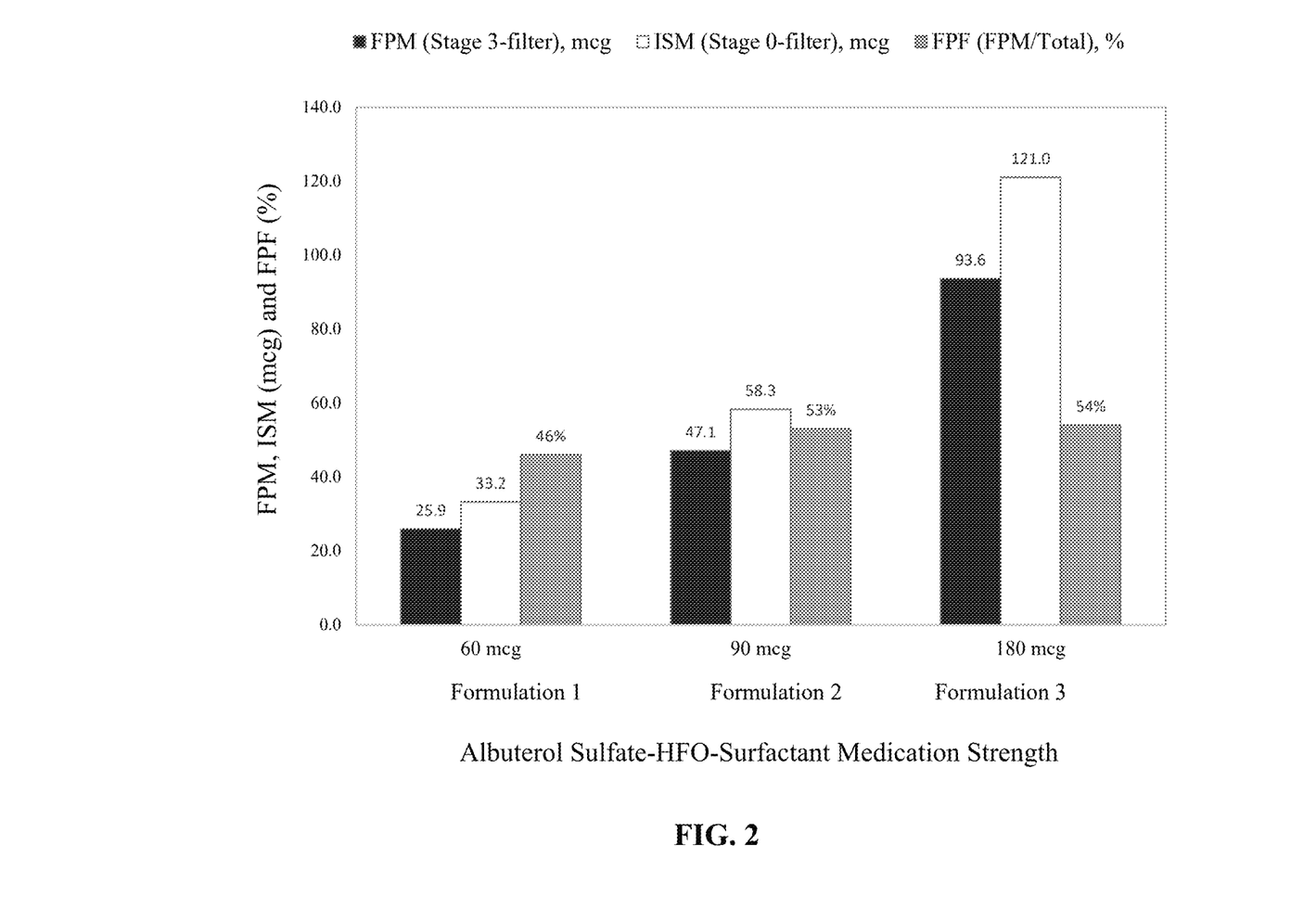
FIG. 2 is a chart showing a comparison of inhalable albuterol sulfate/HFO-1234ze(E) formulations with dose strengths of 60 mcg, 90 mcg, or 180 mcg by fine particle mass (FPM), impactor-sized mass (ISM), and fine particle fraction (FPF) of in vitro Andersen Cascade Impaction evaluation.

| Product | Ventolin HFA | Formulation 2 | Formulation 11 | Formulation 14 | Formulation 16 |
|---|---|---|---|---|---|
| Propellant | HFA 134a | HFO-1234ze(E) | HFO-1234ze(E) | HFO-1234ze(E) | HFO-1234ze(E) |
| Surfactant | None | 0.01% w/w T80 | 0.01% w/w PEG 1000 | 0.01% w/w Span 85 | 0.001% w/w PVP K25 |
| Strength, μg | 90 | 90 | 90 | 90 | 90 |
| Andersen Cascade Impactor Summary, Mass, μg | | | | | |
| Total | 86.3 | 88.3 | 85.0 | 91.2 | 86.9 |
| FPM (Stage 3-filter) | 38.4 | 47.1 | 49.2 | 42.2 | 55.2 |
| ISM (Stage 0-filter) | 43.0 | 58.3 | 58.7 | 51.1 | 63.9 |
| FPF (FPM/Total), % | 44% | 53% | 58% | 46% | 64% |
| MMAD, μm | 2.68 | 3.24 | 3.17 | 3.17 | 2.97 |
| GSD | 1.58 | 1.57 | 1.49 | 1.53 | 1.52 |
| Emitted Dose, μg | | | | | |
| SAC | 86.1 ± 6.9 | 87.0 ± 4.7 | 89.2 ± 3.2 | 92.2 ± 10.9 | 87.7 ± 6.1 | b. Respirable Drug Delivery Assessment of Albuterol Sulfate/HFO-1234Ze(E)/T80 Formulations with Doses of 60 μm, 90 μg, or 180 μg Albuterol sulfate HFO MDI formulations with doses of 60 μg, 90 μg, and 180 μg were assessed for their particle size distribution by Andersen Cascade Impactor analysis and dose content uniformity. Data is summarized in Table 4 and shown in FIG. 2. The data in FIG. 2 demonstrate that both FPM and ISM increase when dose strength increases, and FPF, a measure of the formulation's drug delivery efficiency, is similar to each other.

TABLE 4

In vitro Respirable Drug Delivery Assessment of Albuterol Inhalation in HFO-1234ze(E) with dose strengths of 60 mcg, 90 mcg, or 180 mcg

| Product | Formulation 1 | Formulation 2 | Formulation 3 |
|---|---|---|---|
| Formulation | 0.24% w/w AS + 0.01% T80 + 99.75% HFO-1234ze(E) | 0.36% w/w AS + 0.01% T80 + 99.63% HFO-1234ze(E) | 0.72% w/w AS + 0.05% T80 + 99.23% HFO-1234ze(E) |
| Strength, μg | 60 mcg | 90 mcg | 180 mcg |
| Andersen Cascade Impactor Data, Mass, μg | | | |
| CPM (Throat-Stage 2) | 30.4 | 41.2 | 78.7 |
| FPM (Stage 3-filter) | 25.9 | 47.1 | 93.6 |
| EPM (Stage 6-filter) | 0.9 | 1.9 | 2.0 |
| ISM (Stage 0-filter) | 33.2 | 58.3 | 121.0 |
| FPF (FPM/Total), % | 46% | 53% | 54% |
| MMAD, μm | 3.20 | 3.24 | 3.59 |
| GSD | 1.78 | 1.57 | 1.47 |
| Emitted Dose, μg | | | |
| SAC | 60.6 ± 5.4 | 87.0 ± 4.7 | 179.1 ± 6.2 |

*AS, Albuterol Sulfate c. Effects of Different Surfactants in Albuterol HFO-1234Ze(E) Formulations on Respirable Drug Delivery A small amount of surfactant was added to improve albuterol sulfate particle dispersion in HFO-1234ze(E), enhance the suspension's physical stability, prevent drug particle aggregation, and help lubricate the dosing valve. Several surfactants, such as polysorbate 80 (polyoxyethylene (20) sorbitan monooleate), polysorbate 20 (polyoxyethylene (20) sorbitan monolaurate), PEG 1000, span 85 (sorbitan trioleate), and PVP K25, exhibited certain solubility in HFO-1234ze(E) and showed homogenous phase and were able to be applied to the albuterol sulfate/HFO suspension formulation development. See Table 2 above for the formulations. The Andersen Cascade Impaction data and SAC data of albuterol sulfate formulations with the surfactants of T80, PEG 1000, span 85 (sorbitan trioleate), and PVP K25 are summarized in Tables 5, 6, 7, and 8, respectively.

Figure 3:
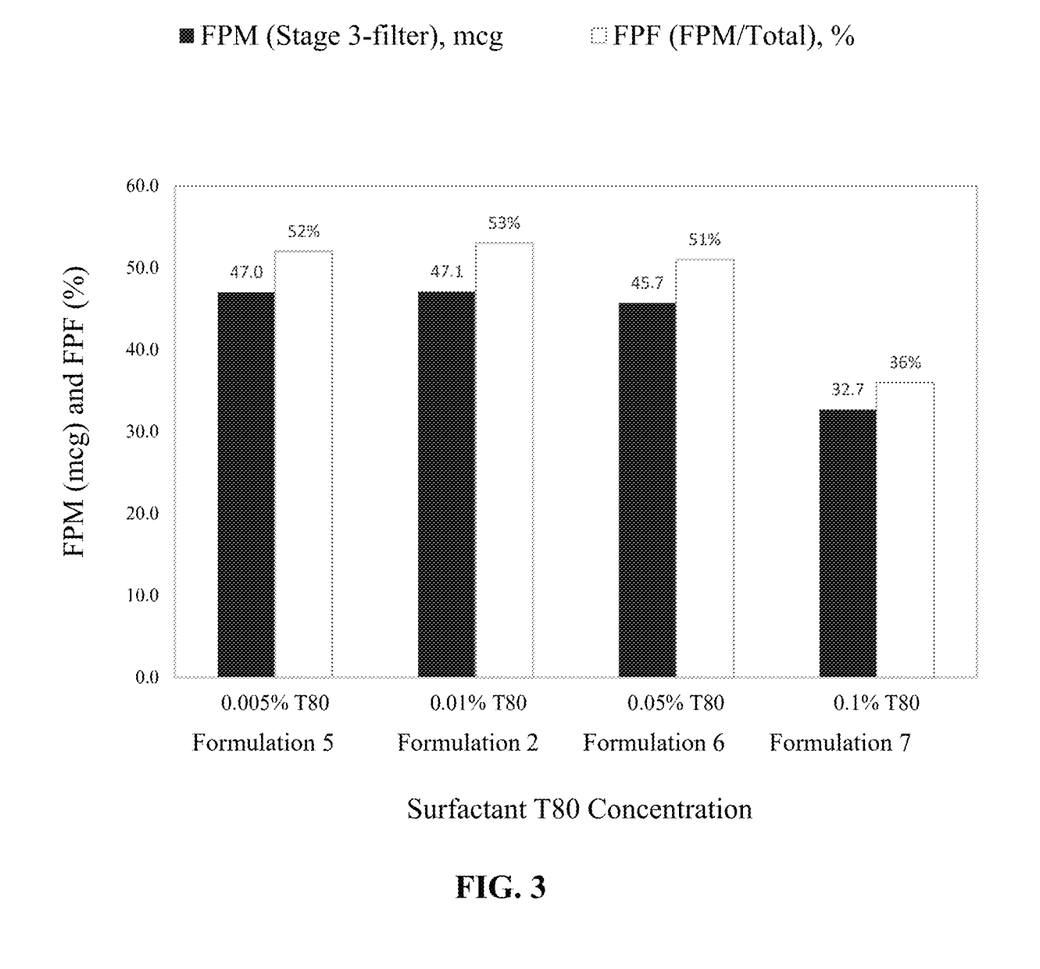
FIG. 3 is a chart showing a comparison of inhalable albuterol sulfate/HFO-1234ze(E) formulations with surfactant polysorbate 80 (polyoxyethylene (20) sorbitan monooleate) (T80) amount of 0.005% w/w to 0.1% w/w by FPM and FPF of in vitro Andersen Cascade Impaction evaluation.

Table 5 presents in vitro data of albuterol sulfate/HFO MDI with the surfactant T80 or T20. The FPFs (showing respirable drug delivery efficiency) of the formulations with 0.005%-0.05% w/w T80 (Formulations 5, 2a, and 6) or with 0.01% w/w T20 (Formulation 2b) are about 51%-55%, which is comparable to or greater than that of Ventolin HFA with an FPF of 44%. However, as the surfactant T80 concentration was increased from 0.05% w/w to 0.1% w/w, a significant decrease of FPM and FPF was observed, along with a much higher throat deposition and CPM than other formulations, see FIG. 3, which also led to a much bigger MMAD. The explanation is that the increase of the surfactant in propellant led to reduced vapor pressures, higher viscosity, and a reduction of atomization energy at the nozzle of the actuator. Consequently, more drug was deposited in the simulated throat and less was delivered into lower stages with a particle size less than or equal to 4.7 μm, hence a reduced FPF and FPM. The data in Table 5 indicates that 0.005%-0.05% w/w of T80 is ideal for an albuterol sulfate/HFO suspension formulation.

TABLE 5

In vitro Respirable Drug Delivery Assessment of Albuterol Inhalation in HFO-1234ze(E)/
Polysorbate 80 (T80) and in HFO-1234ze(E)/Polysorbate 20 (T20)

| | | Product | | | | |
|---|---|---|---|---|---|---|
| | | Formulation 5 | Formulation 2a | Formulation 6 | Formulation 7 | Formulation 2b |
| Propellant | | HFO-1234ze(E) | | | | |
| Surfactant, w/w | | 0.005% T80 | 0.01% T80 | 0.05% T80 | 0.1% T80 | 0.01% T20 |
| Strength, µg | | 90 | 90 | 90 | 90 | 90 |
| | | Andersen Cascade Impactor Data, Mass, µg | | | | |
| Total (Throat-filter) | Aerosol Particle Size | 90.3 | 88.3 | 90.2 | 91.9 | 86.5 |
| Throat | | 33.5 | 30.0 | 28.9 | 41.4 | 29.0 |
| CPM (Throat-Stage 2) | >4.7 µm | 43.3 | 41.2 | 44.4 | 59.3 | 39.1 |
| FPM (Stage 3-filter) | ≤4.7 µm | 47.0 | 47.1 | 45.7 | 32.7 | 47.4 |
| EPM (Stage 6-filter) | ≤1.1 µm | 1.8 | 1.9 | 1.4 | 0.7 | 1.7 |
| ISM (Stage 0-filter) | | 56.8 | 58.3 | 61.2 | 50.5 | 57.5 |
| FPF (FPM/Total), % | | 52% | 53% | 51% | 36% | 55% |
| MMAD, µm | | 3.11 | 3.24 | 3.52 | 4.14 | 3.22 |
| GSD | | 1.57 | 1.57 | 1.77 | 1.66 | 1.52 |
| | | Emitted Dose, µg | | | | |
| SAC | | 89.5 ± 9.0 | 87.0 ± 4.7 | 91.7 ± 4.6 | 91.9 ± 1.3 | 91.9 ± 6.1 |

Table 6 shows the in vitro data of albuterol sulfate/HFO MDI with the surfactant PEG 1000. When PEG 1000 is 0.1% w/w (Formulation 13), the FPF is 4200. However, when the PEG 1000 amount is between 0.005% and 0.02% w/w (Formulations 10-12), the FPF is above 50%.

TABLE 6

In vitro Respirable Drug Delivery Assessment of Albuterol Inhalation in HFO-1234ze(E)/PEG 1000

| Product | | Formulation 10 | Formulation 11 | Formulation 12 | Formulation 13 |
|---|---|---|---|---|---|
| Propellant | | HFO-1234ze(E) | | | |
| Surfactant, w/w | | 0.005% w/w PEG 1000 | 0.01% w/w PEG 1000 | 0.02% w/w PEG 1000 | 0.1% w/w PEG 1000 |
| Strength, µg | | 90 | 90 | 90 | 90 |
| | | Andersen Cascade Impactor Data, Mass, µg | | | |
| Total (Throat-filter) | Aerosol Particle Size | 90.0 | 85.0 | 89.2 | 89.1 |
| Throat | | 32.7 | 26.3 | 26.0 | 35.9 |
| CPM (Throat-Stage 2) | >4.7 µm | 40.9 | 35.8 | 40.5 | 51.5 |
| FPM (Stage 3-filter) | ≤4.7 µm | 49.1 | 49.2 | 48.7 | 37.6 |
| EPM (Stage 6-filter) | ≤1.1 µm | 2.3 | 2.3 | 1.9 | 1.0 |
| ISM (Stage 0-filter) | | 57.3 | 58.7 | 63.2 | 53.2 |
| FPF (FPM/Total), % | | 55% | 58% | 55% | 42% |
| MMAD, µm | | 3.00 | 3.17 | 3.41 | 3.66 |
| GSD | | 1.52 | 1.49 | 1.62 | 1.95 |
| | | Emitted Dose, µg | | | |
| SAC | | 86.3 ± 8.7 | 89.2 ± 3.4 | 92.2 ± 6.8 | 86.2 ± 10.9 |

Table 7 shows the in vitro data of albuterol sulfate/HFO MDI with the surfactant span 85 (sorbitan trioleate). The FPF of Formulation 14 (0.01% w/w span 85 (sorbitan trioleate)) is 46%, and the FPF of Formulation 15 (0.05% w/w span 85 (sorbitan trioleate)) is 35%.

TABLE 7

In vitro Respirable Drug Delivery Assessment of Albuterol Inhalation in HFO-1234ze(E)/Span85

| Product | | Formulation 14 | Formulation 15 |
|---|---|---|---|
| Propellant | | HFO-1234ze(E) | |
| Surfactant, w/w | | 0.01% Span 85 | 0.05% Span 85 |
| Strength, µg | | 90 | 90 |
| Andersen Cascade Impactor Data, Mass, µg | | | |
| Total (Throat-filter) | Aerosol Particle Size | 91.2 | 85.4 |
| Throat | | 40.1 | 40.9 |
| CPM (Throat-Stage 2) | >4.7 µm | 49.0 | 55.8 |
| FPM (Stage 3-filter) | ≤4.7 µm | 42.2 | 29.6 |
| EPM (Stage 6-filter) | ≤1.1 µm | 1.2 | 0.7 |
| ISM (Stage 0-filter) | | 51.1 | 44.5 |
| FPF (FPM/Total), % | | 46% | 35% |
| MMAD, µm | | 3.17 | 4.03 |
| GSD | | 1.53 | 1.62 |
| Emitted Dose, µg | | | |
| SAC | | 92.2 ± 10.9 | 84.4 ± 14.0 |

Table 8 shows the in vitro data of albuterol sulfate/HFO MDI with the surfactant PVP K25. The FPFs of example 1 Formulations 16 and 17 are at least 60% at 0.001%-0.005% w/w of PVP K25.

TABLE 8

In vitro Respirable Drug Delivery Assessment of Albuterol Inhalation in HFO-1234ze(E)/PVP K25

| Product | | Formulation 16 | Formulation 17 |
|---|---|---|---|
| Propellant | | HFO-1234ze(E) | |
| Surfactant, w/w | | 0.001% PVP K25 | 0.005% PVP K25 |
| Strength, µg | | 90 | 90 |
| Andersen Cascade Impactor Data, Mass, µg | | | |
| Total (Throat-filter) | Aerosol Particle Size | 86.9 | 86.4 |
| Throat | | 23.0 | 25.0 |
| CPM (Throat-Stage 2) | >4.7 µm | 31.7 | 34.9 |
| FPM (Stage 3-filter) | ≤4.7 µm | 55.2 | 51.5 |
| EPM (Stage 6-filter) | ≤1.1 µm | 3.3 | 4.0 |
| ISM (Stage 0-filter) | | 63.9 | 61.4 |
| FPF (FPM/Total), % | | 64% | 60% |
| MMAD, µm | | 2.97 | 2.91 |
| GSD | | 1.52 | 1.62 |
| Emitted Dose, µg | | | |
| SAC | | 89.0 ± 3.4 | 94.6 ± 4.1 |

While the invention has been described and illustrated herein by references to various specific materials, procedures, and examples, it is understood that the invention is not restricted to the combinations of materials and procedures selected for that purpose. Numerous variations of such details can be implied as will be appreciated by those skilled in the art. It is intended that the specification and examples be considered as exemplary, only, with the true scope and spirit of the invention being indicated by the following claims. All references, patents, and patent applications referred to in this application are herein incorporated by reference in their entirety.

What is claimed is:

1. A co-solvent-free pharmaceutical aerosol formulation for use with a pressurized metered dose inhaler (MDI) comprising:
   (a) a suspension formulation of pre-micronized albuterol sulfate or other pharmaceutically acceptable salt, or albuterol base thereof;
   (b) a pressurized, liquefied propellant comprising a hydrofluoroolefin (HFO) present in an amount of from about 99.0% to about 99.9% (w/w) relative to the total weight of the formulation; and
   (c) a surfactant in an amount not more than about 0.1% (w/w) relative to the total weight of the formulation,
   wherein the formulation does not contain a co-solvent selected from the group of ethanol, glycerol, propylene glycol, and a combination thereof.

2. The co-solvent-free pharmaceutical aerosol formulation of claim 1, wherein the pre-micronized albuterol sulfate or a pharmaceutically acceptable salt, or albuterol base thereof has a particle size in a range of less than 5 µm in diameter and/or is present in an amount of from about 0.10% to about 0.80% (w/w) relative to the total weight of the formulation.

3. The co-solvent-free pharmaceutical aerosol formulation of claim 1, wherein the formulation is configured to deliver an albuterol dose strength in an amount from about 60 mcg to about 200 mcg per actuation of the pressurized metered dose inhaler.

4. The co-solvent-free pharmaceutical aerosol formulation of claim 1, wherein the liquefied propellant comprises trans-1,3,3,3-tetrafluoropropene (HFO-1234ze(E)).

5. A co-solvent-free pharmaceutical aerosol formulation for use with a pressurized metered dose inhaler (MDI) comprising:
   (a) a suspension formulation of pre-micronized albuterol sulfate or other pharmaceutically acceptable salt, or albuterol base thereof;
   (b) a pressurized, liquefied propellant comprising a hydrofluoroolefin (HFO) present in an amount of from about 99.0% to about 99.9% (w/w) relative to the total weight of the formulation; and
   (c) a surfactant in an amount not more than about 0.1% (w/w) relative to the total weight of the formulation,
   wherein the formulation does not contain any co-solvent.

6. The co-solvent-free pharmaceutical aerosol formulation of claim 1, wherein the surfactant is selected from the group consisting of a polysorbate, a polyethylene glycol, a sorbitan ester, a polyvinylpyrrolidone, or a combination thereof.

7. The co-solvent-free pharmaceutical aerosol formulation of claim 6, wherein the surfactant comprises polyoxyethylene (20) sorbitan monooleate or polyoxyethylene (20) sorbitan monolaurate.

8. The co-solvent-free pharmaceutical aerosol formulation of claim 7, wherein the surfactant comprises polyoxyethylene (20) sorbitan monooleate.

9. The co-solvent-free pharmaceutical aerosol formulation of claim 7, wherein the polyoxyethylene (20) sorbitan monooleate or polyoxyethylene (20) sorbitan monolaurate is present in an amount of not more than 0.1% (w/w) relative to the total weight of the formulation.

10. The co-solvent-free pharmaceutical aerosol formulation of claim 6, wherein the polyethylene glycol is PEG 1000, and is present in an amount of not more than 0.1% (w/w) relative to the total weight of the formulation.

11. The co-solvent-free pharmaceutical aerosol formulation of claim 6, wherein the sorbitan ester is sorbitan trioleate and is present in an amount of not more than 0.05% (w/w) relative to the total weight of the formulation.

12. The co-solvent-free pharmaceutical aerosol formulation of claim 6, wherein the polyvinylpyrrolidone is polyvinylpyrrolidone K25 and is present in an amount of not more than 0.005% (w/w) relative to the total weight of the formulation.

13. The co-solvent-free pharmaceutical aerosol formulation of claim 1 comprising:
   (a) a suspension formulation of pre-micronized albuterol sulfate or a pharmaceutically acceptable salt, or albuterol base thereof, in an amount of from about 0.10% to about 0.80% (w/w) relative to the total weight of the formulation;
   (b) HFO-1234ze(E) present in an amount of 99.0% to 99.9% (w/w) relative to the total weight of the formulation; and
   (c) polyoxyethylene (20) sorbitan monooleate or polyoxyethylene (20) sorbitan monolaurate in an amount not more than 0.1% (w/w) relative to the total weight of the formulation.

14. The co-solvent-free pharmaceutical aerosol formulation of claim 13 comprising:
   (a) a suspension formulation of pre-micronized albuterol sulfate or a pharmaceutically acceptable salt, or albuterol base thereof in an amount of from about 0.16% to about 0.40% (w/w) relative to the total weight of the formulation;
   (b) HFO-1234ze(E) present in an amount of from about 99.5% to about 99.8% (w/w) relative to the total weight of the formulation; and
   (c) polyoxyethylene (20) sorbitan monooleate or polyoxyethylene (20) sorbitan monolaurate in an amount not more than 0.05% (w/w) relative to the total weight of the formulation.

15. The co-solvent-free pharmaceutical aerosol formulation of claim 1 comprising:
   (a) a suspension formulation of pre-micronized albuterol sulfate or a pharmaceutically acceptable salt, or albuterol base thereof in an amount of from about 0.10% to about 0.80% (w/w) relative to the total weight of the formulation;
   (b) HFO-1234ze(E) present in an amount of 99.0% to 99.9% (w/w) relative to the total weight of the formulation; and
   (c) PEG 1000 in an amount not more than 0.1% (w/w) relative to the total weight of the formulation.

16. The co-solvent-free pharmaceutical aerosol formulation of claim 15 comprising:
   (a) a suspension formulation of pre-micronized albuterol sulfate or a pharmaceutically acceptable salt, or albuterol base thereof in an amount of from about 0.16% to about 0.40% (w/w) relative to the total weight of the formulation;
   (b) HFO-1234ze(E) present in an amount of from about 99.5% to about 99.8% (w/w) relative to the total weight of the formulation; and
   (c) PEG 1000 in an amount not more than 0.02% (w/w) relative to the total weight of the formulation.

17. The co-solvent-free pharmaceutical aerosol formulation of claim 1 comprising:
   (a) a suspension formulation of pre-micronized albuterol sulfate or a pharmaceutically acceptable salt, or albuterol base thereof in an amount of from about 0.10% to about 0.80% (w/w) relative to the total weight of the formulation;
   (b) HFO-1234ze(E) present in an amount of 99.0% to 99.9% (w/w) relative to the total weight of the formulation; and
   (c) sorbitan trioleate in an amount not more than 0.05% (w/w) relative to the total weight of the formulation.

18. The co-solvent-free pharmaceutical aerosol formulation of claim 17 comprising:
   (a) a suspension formulation of pre-micronized albuterol sulfate or a pharmaceutically acceptable salt, or albuterol base thereof in an amount of from about 0.16% to about 0.40% (w/w) relative to the total weight of the formulation;
   (b) HFO-1234ze(E) present in an amount of 99.5% to about 99.8% (w/w) relative to the total weight of the formulation; and
   (c) sorbitan trioleate in an amount not more than 0.01% (w/w) relative to the total weight of the formulation.

19. The co-solvent-free pharmaceutical aerosol formulation of claim 1 comprising:
   (a) a suspension formulation of pre-micronized albuterol sulfate or a pharmaceutically acceptable salt, or albuterol base thereof in an amount of from about 0.10% to about 0.80% (w/w) relative to the total weight of the formulation;
   (b) HFO-1234ze(E) present in an amount of 99.0% to 99.9% (w/w) relative to the total weight of the formulation; and
   (c) polyvinylpyrrolidone K25 in an amount not more than 0.005% (w/w) relative to the total weight of the formulation.

20. The co-solvent-free pharmaceutical aerosol formulation of claim 19 comprising:
   (a) a suspension formulation of pre-micronized albuterol sulfate or a pharmaceutically acceptable salt, or albuterol based thereof in an amount of from about 0.16% to about 0.40% (w/w) relative to the total weight of the formulation;
   (b) HFO-1234ze(E) present in an amount of 99.5% to 99.8% (w/w) relative to the total weight of the formulation; and
   (c) polyvinylpyrrolidone K25 in an amount not more than 0.005% (w/w) relative to the total weight of the formulation.

* * * * *